(12) United States Patent
Neal et al.

(10) Patent No.: US 10,149,613 B2
(45) Date of Patent: Dec. 11, 2018

(54) WAVEFRONT INTERACTIVE REFRACTION DISPLAY

(71) Applicant: AMO WaveFront Sciences, LLC, Santa Ana, CA (US)

(72) Inventors: Daniel R. Neal, Tijeras, NM (US); Stephen W. Farrer, Albuquerque, NM (US); Larry B. Voss, Tijeras, NM (US); Thomas D. Raymond, Edgewood, NM (US); Daniel R. Hamrick, Cedar Crest, NM (US); John G. Dixson, Albuquerque, NM (US); Phillip Riera, Albuquerque, NM (US); Ron R. Rammage, Tijeras, NM (US); Richard J. Copland, Albuquerque, NM (US)

(73) Assignee: AMO Wavefront Sciences, LLC, Santa Ana, CA (US)

( * ) Notice: Subject to any disclaimer, the term of this patent is extended or adjusted under 35 U.S.C. 154(b) by 0 days.

(21) Appl. No.: 15/654,534

(22) Filed: Jul. 19, 2017

(65) Prior Publication Data

US 2017/0311798 A1 Nov. 2, 2017

Related U.S. Application Data

(63) Continuation of application No. 14/996,112, filed on Jan. 14, 2016, now Pat. No. 9,713,421, which is a continuation of application No. 14/199,702, filed on Mar. 6, 2014, now Pat. No. 9,271,646.

(60) Provisional application No. 61/799,764, filed on Mar. 15, 2013.

(51) Int. Cl.
*A61B 3/10* (2006.01)
*A61B 3/00* (2006.01)
*A61B 3/103* (2006.01)

(52) U.S. Cl.
CPC ............ *A61B 3/103* (2013.01); *A61B 3/0025* (2013.01); *A61B 3/0033* (2013.01); *A61B 3/0041* (2013.01); *A61B 3/0091* (2013.01); *A61B 3/1015* (2013.01)

(58) Field of Classification Search
CPC ..... A61B 3/103; A61B 3/1015; A61B 3/0091; A61B 3/14; A61B 3/1005
USPC ........................................................ 351/211
See application file for complete search history.

(56) References Cited

U.S. PATENT DOCUMENTS

| | | | |
|---|---|---|---|
| 5,963,300 A | 10/1999 | Horwitz | |
| 6,413,251 B1 * | 7/2002 | Williams | ............ A61F 9/00806 128/898 |
| 6,500,171 B1 | 12/2002 | Williams et al. | |

FOREIGN PATENT DOCUMENTS

| | | |
|---|---|---|
| WO | 0167977 A1 | 9/2001 |
| WO | 2012154278 A1 | 11/2012 |

OTHER PUBLICATIONS

International Search Report and Written Opinion for Application No. PCT/US2014/021339, dated Jun. 23, 2014, 12 pages.

* cited by examiner

*Primary Examiner* — Mohammed Hasan
(74) *Attorney, Agent, or Firm* — Johnson & Johnson Surgical Vision, Inc.

(57) ABSTRACT

Embodiments of this invention generally relate to systems and methods for wavefront interactive refraction display and more particularly to systems and methods for capturing and displaying eye wavefront interactive refraction data based on the desired refractive state of the patient's eye.

20 Claims, 9 Drawing Sheets

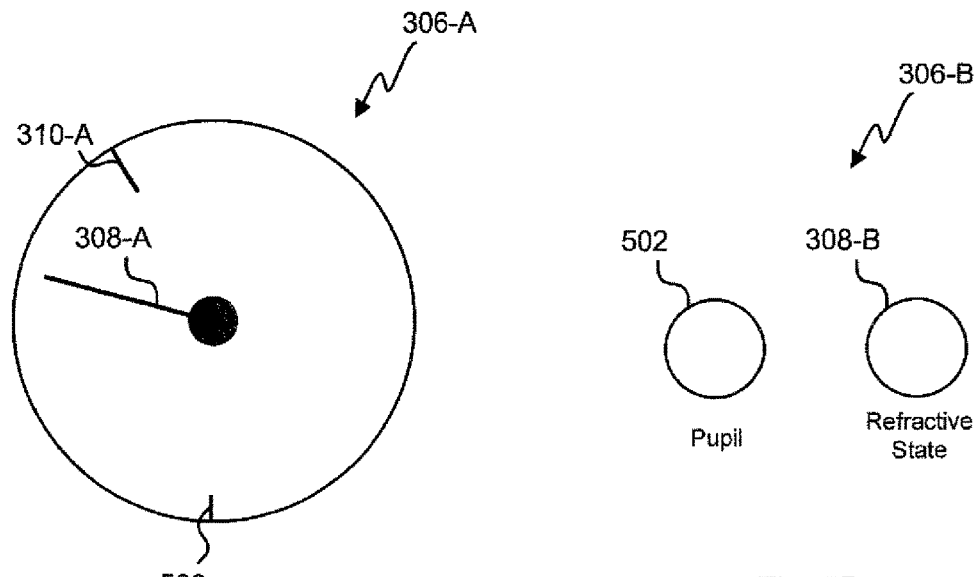
Fig. 5A
Fig. 5B
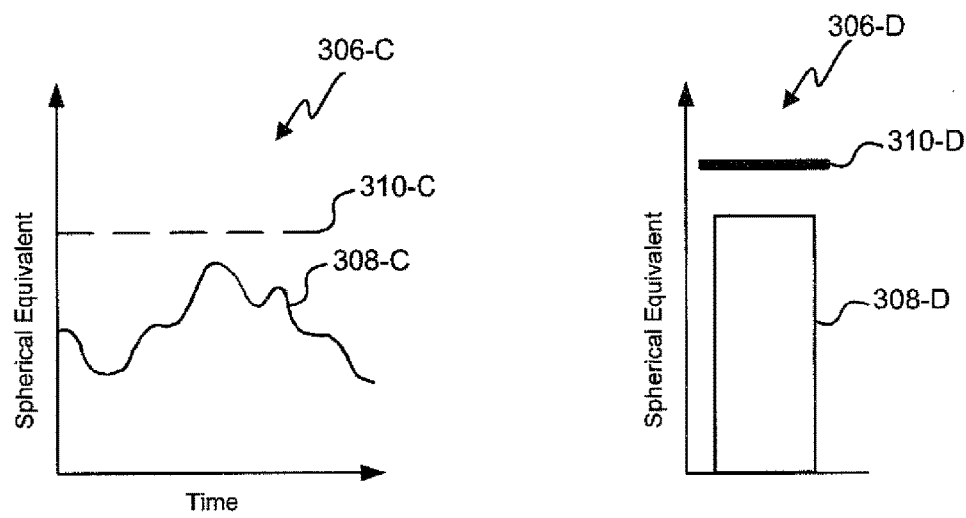
Fig. 5C
Fig. 5D

900

| Tasks |
|---|
| • Grip Handle |
| • Imagine |
| • Mental Game |
| • Identify Change |
| • Identify Words/Images |
| • Target Game |

| Target Changes |
|---|
| • Image |
| • Feature |
| • Color |
| • Shape |
| • Contrast |
| • Brightness |
| • Brightness/Position |
| • Brightness/Focus |
| • Focus |
| • Video |

Fig. 10

WAVEFRONT INTERACTIVE REFRACTION DISPLAY

CROSS-REFERENCES TO RELATED APPLICATIONS

This application is a continuation of and claims priority to U.S. patent application Ser. No. 14/996,112, filed on Jan. 14, 2016, Now U.S. Pat. No. 9,713,421 B2 which is a continuation of and claims priority to U.S. patent application Ser. No. 14/199,702, filed Mar. 6, 2014 and issued on Mar. 1, 2016 as U.S Pat. No. 9,271,646, which claims priority to U.S. Provisional Application No. 61/799,764, filed on Mar. 15, 2013, the entire contents of each of which are incorporated herein by reference.

FIELD OF THE INVENTION

Embodiments of the present invention generally relate to wavefront interactive refraction display and more particularly to systems and methods that capture and display eye wavefront interactive refraction data.

BACKGROUND OF THE INVENTION

Refractive measurements of the eye should occur with the accommodation of the eye fully relaxed. To accomplish this, aberrometers move an internal visual target to draw the eye to its farthest focus. Then a final refractive measurement is made. When the target is at the optimal position, the target is "fogged" and it always appears slightly fuzzy to the patient. However, sometimes the eye does not respond to the target, and the final refractive measurement can occur with the eye partially accommodated. When this happens, the patient is said to exhibit "instrument myopia" and the target may either appear clear or fuzzy to the patient.

While most people respond reliably to the target inside an aberrometer, some patients persistently exhibit instrument myopia. Repeated measurements can fatigue the eye and the patient can exhibit increasing instrument myopia.

When patients are screened for LASIK treatment, they are measured both with a manifest refraction and with an aberrometer. Typically the manifest refraction is done first, and then the results are entered into the aberrometer software. If the wavefront and manifest refractions agree within some tolerance, the patient may be treated with wavefront guided LASIK. However, if the measurements disagree, the patient can only be treated with standard LASIK, based on the manifest refraction alone.

To ensure the greatest number of patients qualify for wavefront guided LASIK, the aberrometer should minimize instrument myopia, or provide some means to help the doctor to get the patient to relax their accommodation.

Doctors have a number of techniques they can use to coax a patient into relaxing accommodation. For instance, they can distract a patient by telling them to grip a handle, or mentally subtract two numbers. However, when the doctor employs such a technique, a standard measurement follows without any interactive feedback. Consequently the doctor has to wait many seconds to see if the desired effect occurred. If the effect of the coaxing was transitory, the software will still produce a measurement with instrument myopia. Also, coaxing takes time. Prolonged measurement sessions tend to fatigue the eye and often results in the patient showing increasing instrument myopia.

SUMMARY OF THE INVENTION

The field of the invention relates to systems and methods for wavefront interactive refraction display and more particularly to systems and methods that capture and display eye wavefront interactive refraction data. In an embodiment, a method for identifying a time for capturing eye refraction data includes sensing a waveform of light passing through a patient's eye over a period of time, wherein the waveform is affected by an optical property of the patient's eye, calculating the refractive state of the patient's eye with the sensed waveform, displaying an indication of the current refractive state of the patient's eye, receiving a command to capture eye refraction data when the desired refractive state of the patient's eye is reached, and capturing eye refraction data.

Further areas of applicability of the present disclosure will become apparent from the detailed description provided hereinafter. It should be understood that the detailed description and specific examples, while indicating various embodiments, are intended for purposes of illustration only and are not intended to necessarily limit the scope of the disclosure.

BRIEF DESCRIPTION OF THE DRAWINGS

The present disclosure is described in conjunction with the appended figures:

FIGS. 5A-5D depict embodiments of the graphic display of a refractive state of an eye;

FIG. 9 is a list of exemplary tasks that can be performed in connection with the wavefront interactive refractor; and FIG. 10 is a list of exemplary changes to a target that can be made to affect a change in the refractive state of the patient's eye.

In the appended figures, similar components and/or features may have the same reference label. Where the reference label is used in the specification, the description is applicable to any one of the similar components having the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION OF THE INVENTION

The ensuing description provides preferred exemplary embodiment(s) only, and is not intended to limit the scope, applicability or configuration of the disclosure. Rather, the ensuing description of the preferred exemplary embodiment(s) will provide those skilled in the art with an enabling description for implementing a preferred exemplary embodiment. It is understood that various changes may be made in the function and arrangement of elements without departing from the spirit and scope as set forth in the appended claims.

Wavefronts

A wavefront can be used to describe a wave including, for example, an electromagnetic wave. A wavefront is the locus of points having the same phase, and can be a line or curve in two dimensions, or surface of a wave that is propagating in three dimensions. Wavefront measurements can be used to evaluate the quality of an optical system and/or to identify imperfections in an optical system. In some embodiments, these measurements can be performed by a wavefront sensor which is a device that can measure wavefront aberration in a coherent signal. A Hartmann-Shack system is one embodiment of a wavefront sensor.

Figure 1:
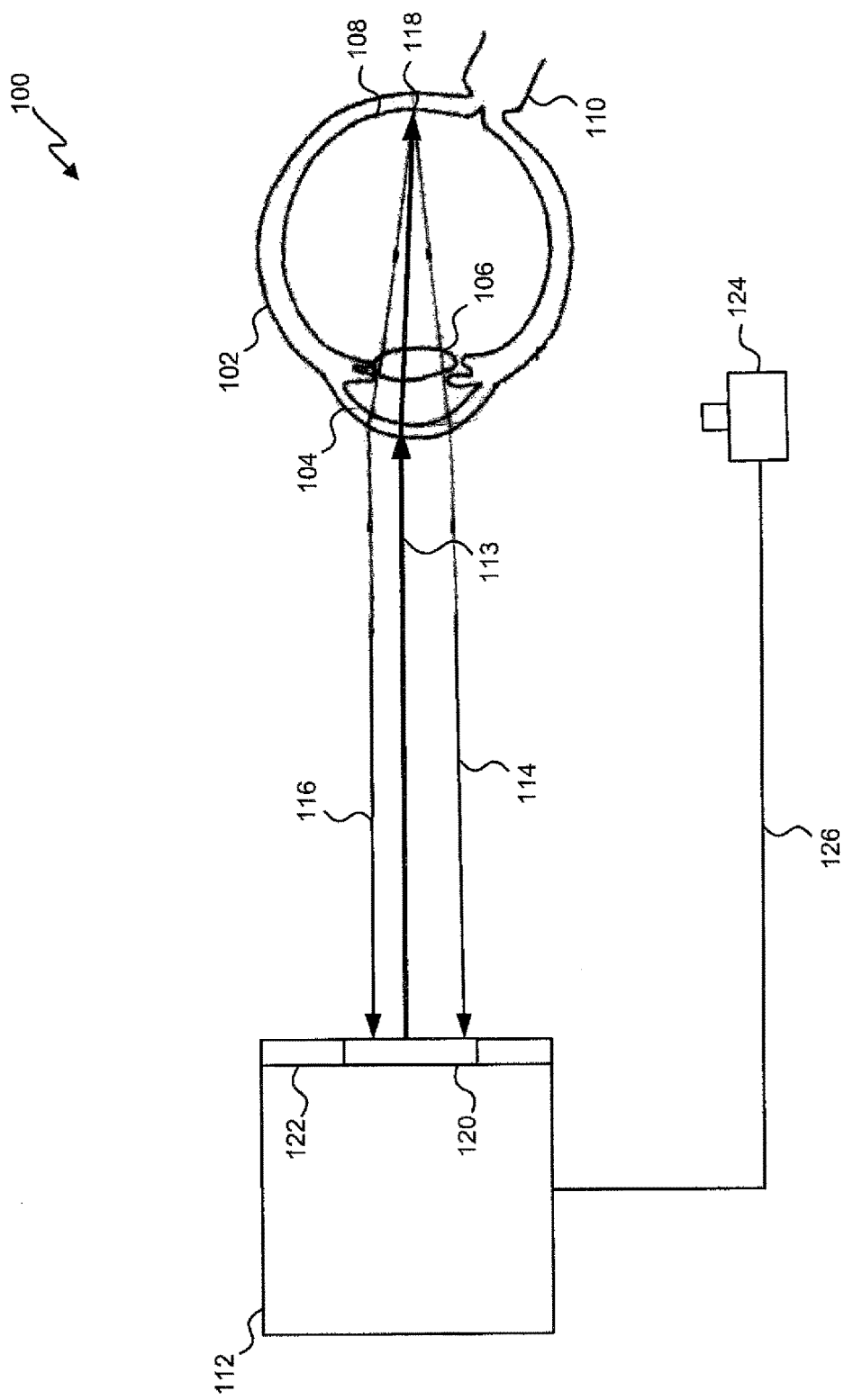
FIG. 1 is a schematic illustration of one embodiment of a wavefront interactive refraction system.

With reference now to FIG. 1, schematic illustration of one embodiment of a wavefront interactive refraction system 100 is shown. The wavefront interactive refraction system 100 can capture data relating to one or several refractive states the patient's eye, and can come in some embodiments be configured to provide information to a user to identify a time at which the refractive state of the patient's eye should be captured, and to capture data corresponding to a desired refractive state of the patient's eye. In some embodiments, information relating to the captured refractive state of the patient eye can be used for determining corrective treatments for the eye, including, for example, determining an appropriate corrective lens and/or an appropriate corrective surgery.

Wavefront interactive refraction display 100 includes an eye 102. The eye 102 can be any eye, and can be, for example, a human eye. The eye 102 includes the cornea 104, the lens 106, the retina 108, and the optic nerve 110.

Wavefront interactive refraction display 100 includes a wavefront interactive refractor 112. Wavefront interactive refractor 112 can be configured to generate data identifying a refractive state of the eye 102. In some embodiments, the wavefront interactive refractor 112 can generate data identifying a refractive state of the eye 102 by sensing a wavefront passing through the eye 102 either towards or away from the retina 108. In the embodiment depicted in FIG. 1, the wavefront interactive refractor directs it being 113 of light onto a portion 118 of the retina 108. In some embodiments, this beam 113 of light can comprise a coherent beam of light that can be configured to reflect off the portion 118 of the retina 108 In some embodiments, the beam 113 can be configured so as not to damage the retina 108 and/or the portion 118 of the retina 108 onto which the beam 113 is directed, and in some embodiments, the theme 113 can comprise a laser.

As seen in FIG. 1, the beam 113 can reflect off the portion 118 of the retina and generate light rays 114, 116 that passed through the lens 106 and the cornea 104 and impinge on the wavefront interactive refractor 112. In some embodiments, when the light rays 114, 116 pass through the lens 106 and the cornea 104 of the eye 102 the wavefront of the light rays 114, 116 can be altered according to the optical properties of the eye 102. The light rays 114, 116 can, in some embodiments, impinge on a sensor 120 of the wavefront interactive refractor 112. The sensor 120 can comprise any desired photodetecting feature, and can, in some embodiments comprise a photodetecting feature that generates and/or captures data relating to the refractive state of the eye 102 including, for example, wavefront data which can be used to determine the refractive state of the eye 102. In some embodiments, the photo-detecting feature can comprise an array of photodetectors and a lenslet array spaced from the array of photodetectors and configured to focus light onto the photodetectors. In some embodiments, the photo-detecting feature can comprise, for example, a Shack-Hartmann system.

In some embodiments, the wavefront interactive refractor 112 can comprise a patient interface that can include a patient output device 122 and a patient input device 124. In some embodiments, the patient output device 122 can provide information to the patient and can be, for example, a display and/or a speaker. In some embodiments, the patient output device 122 can provide information to the patient relating to one or several tasks that the patient can complete. In one embodiment, for example, the patient output device 122 can comprise a display with an image that is viewable by the patient.

The patient input device 124 can comprise any feature configured to allow the patient to provide an input to the wavefront interactive refractor 112. In some embodiments, the patient input device 124 can comprise a button, a key, a keypad, a microphone, or a sensor. The patient can, in some embodiments, use the patient input device 124 to complete the task which can include, for example, depressing a button when a specified change in the displayed image occurs.

Figure 2:
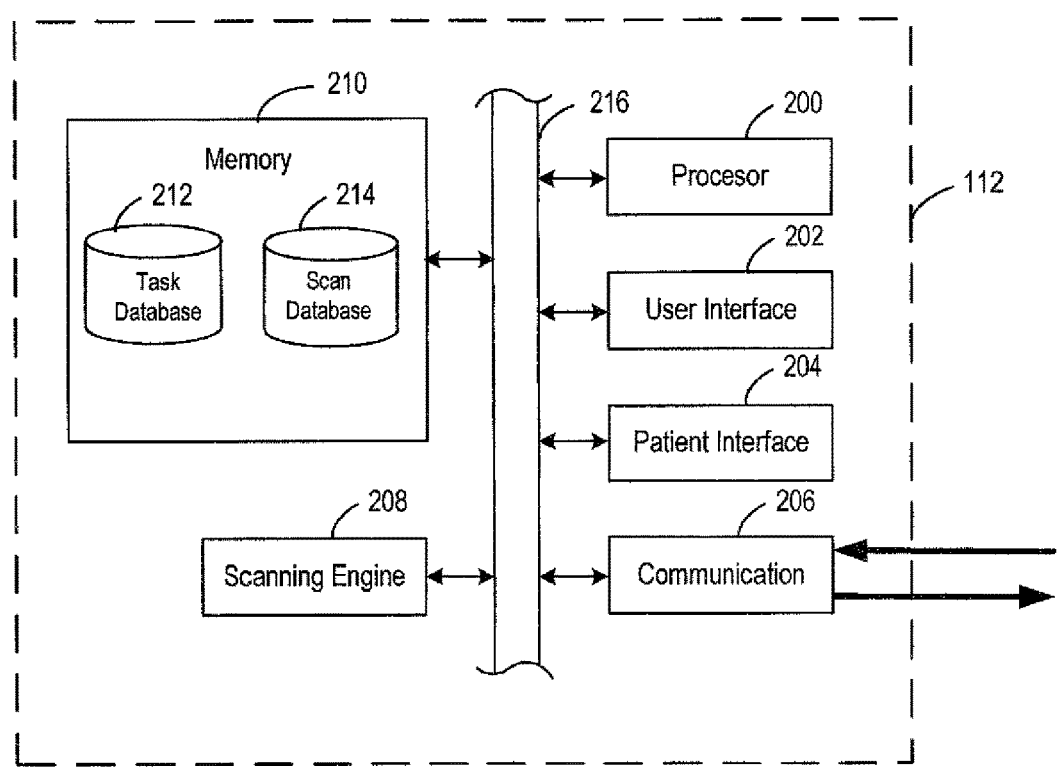
FIG. 2 is a schematic illustration of one embodiment of a wavefront interactive refractor.

With reference now to FIG. 2, schematic illustration of one embodiment of a wavefront interactive refractor 112 is shown. Wavefront interactive refractor 112 includes a processor 200. The processor 200 can provide instructions to, and receive information from the other components of the wavefront interactive refractor 112. The processor 200 can act according to stored instructions to control the other components of the wavefront interactive refractor 112. The processor 200 can comprise a microprocessor, such as a microprocessor from Intel® or Advanced Micro Devices, Inc.®, or the like.

In some embodiments, the processor 200 can be configured to be embedded in the wavefront interactive refractor 112 and to process full wavefront reconstructions. In some embodiments, this processor 200 can comprise a field programmable gate array (FPGA).

The wavefront interactive refractor 112 can include user interface 202. The user interface 202 communicates information, including outputs, to, and receives inputs from a user. The user interface 202 can include a screen, a speaker, a monitor, a keyboard, a microphone, a mouse, a touchpad, a keypad, and/or any other feature or features that can receive inputs from a user and provide information to a user. In some embodiments, the user interface 202 can provide outputs to, and receive inputs from a user including a doctor. In some embodiments, the user interface 202 can be configured to allow the user including the doctor to control the operation of the wavefront interactive refractor 112, and to specifically control the interaction of the wavefront interactive refractor 112 with the patient.

The wavefront interactive refractor 112 can include a patient interface 204. The patient interface 204 communicates information including outputs to a patient and receives information including inputs from a patient. In some embodiments, the patient interface 204 can communicate information to the patient via a patient visual display. The patient visual display can provide visual data to the patient. In some embodiments, the patient visual display can be generated by the patient output device 122, and specifically in embodiments in which the patient output device 122 comprises a display and/or screen, the patient visual display can be shown to the patient by the display and/or screen In some embodiments, the patient interface 204 can be configured to provide a patient with a task and, in some embodiments, to receive inputs corresponding to the patient completion of the task. The patient interface 204 can comprise a screen, a speaker, a button, monitor, a keyboard, a microphone, a mouse, a touchpad, a keypad, and/or any other feature or features that can receive patient inputs and provide information to the patient.

The wavefront interactive refractor 112 can comprise communication engine 206. The communication engine 206 can allow the wavefront interactive refractor 112 to communicatingly connect with other devices, and can allow the wavefront interactive refractor 112 to send and receive information from other devices. The communication engine 206 can include features configured to send and receive information, including, for example, an antenna, a modem, a transmitter, receiver, or any other feature that can send and receive information. The communication engine 206 can communicate via telephone, cable, fiber-optic, or any other wired communication network. In some embodiments, the communication engine 206 can communicate via cellular networks, WLAN networks, or any other wireless network.

The wavefront interactive refractor 112 includes a scanning engine 208. In some embodiments, for example, the scanning engine 208 can be configured to generate data corresponding to the refraction state of the patient's eye 102. In some embodiments, for example, the scanning engine 208 can be configured to generate the beam 113, and to direct the beam 113 onto the retina 108 of the patient's eye 102. In some embodiments, the scanning engine 208 can be further configured to capture the light rays 114, 116 reflecting off the retina 108 of the patient's eye 102 and passing through the lens 106 and the cornea 104 of the patient's eye 102. In some embodiments, the scanning engine 208 can be configured to generate data corresponding to the wavefront of the light rays 114, 116 and/or of the light passing through the patient's eye 102, which data can be used to determine the refractive state of the patient's eye 102.

In some embodiments, the scanning engine 208 can comprise a camera and can be configured to capture image data of the eye 102. In some embodiments, image data for one or several images captured by the scanning engine 208 can be stored and used to generate a full wavefront reconstruction of the eye 102.

In some embodiments, the scanning engine 208 can include features configured to perform wavefront analysis on the eye 102, which features can include a wavefront sensor. In one embodiment, the wavefront sensor can be an optical capture device which can be any device with light sensing components and can be, for example, a camera and/or scanner. The wavefront sensor can comprise a plurality of photoreceptors which can be, for example, arranged into a matrix of photoreceptors. The wavefront sensor can further comprise an array of lenslets, mirrors, and/or any other features capable of reflecting and/or refracting light. In one embodiment, each lenslet and/or mirror can be associated with the subset of photoreceptors from the matrix of photoreceptors. In one embodiment, for example, each of the lenslets and/or mirrors can be associated with a group of four photoreceptors. In one embodiment, for example, the wavefront sensor can comprise a Hartmann-Shack system.

The wavefront interactive refractor 112 can include memory 210. The memory 210 can include stored instructions that, when executed by the processor 200, control the operation of the wavefront interactive refractor 112. The details of the memory 210 are discussed at greater length below.

As seen in FIG. 2, the memory 210 can include one or several databases including, for example, a task database 212 and a scan database 214. The task database 212 can include one or several tasks that can be provided to the patient. In some embodiments, the one or several tasks can be used to affect a refractive state of the patient's eye 102. It is believed that a task can serve to distract the patient, which distraction can result in relaxation of the ciliary muscles which can reduce and/or eliminate accommodation in the eye 102. This relaxed accomodative state can allow a more accurate capture of the refractive state of the eye 102. The task can comprise an instruction explaining to the patient what the task is and how to complete the task, a stimulus which can include, for example, any item, image, or thing that is experienced by the patient including, for example, a video, a text string, a question, and/or an input which can be any requested patient action including, for example, applying force to an object and providing an input to the wavefront interactive refractor 112.

In some embodiments, the task database 212 can comprise an index of tasks included in the task database. This index can include, for example, data corresponding to the instruction, the stimulus, and/or desired inputs, and/or user instructions to allow the user to facilitate the completion of the task by the patient.

The scan database 214 can comprise information generated by the scanning engine 208 and/or data related to information generated by the scanning engine 208. In some embodiments, for example, the information generated by the scanning engine 208 can include information identifying the refractive state of the eye 102, information tracking the refractive state of the eye 102 as a function of time, information identifying turning points including, for example, maximums and minimums, and/or inflection points in the data tracking the refractive state of the eye 102 as a function of time, task, and/or pupil size. In some embodiments, the scan database 214 can further include information relating to a patient including, for example, information identifying the patient, information associating a patient with information generated by the scanning engine 208, information associating a patient with previously gathered information relating to the refractive state of the eye, and/or any other desired patient information.

Figure 3:
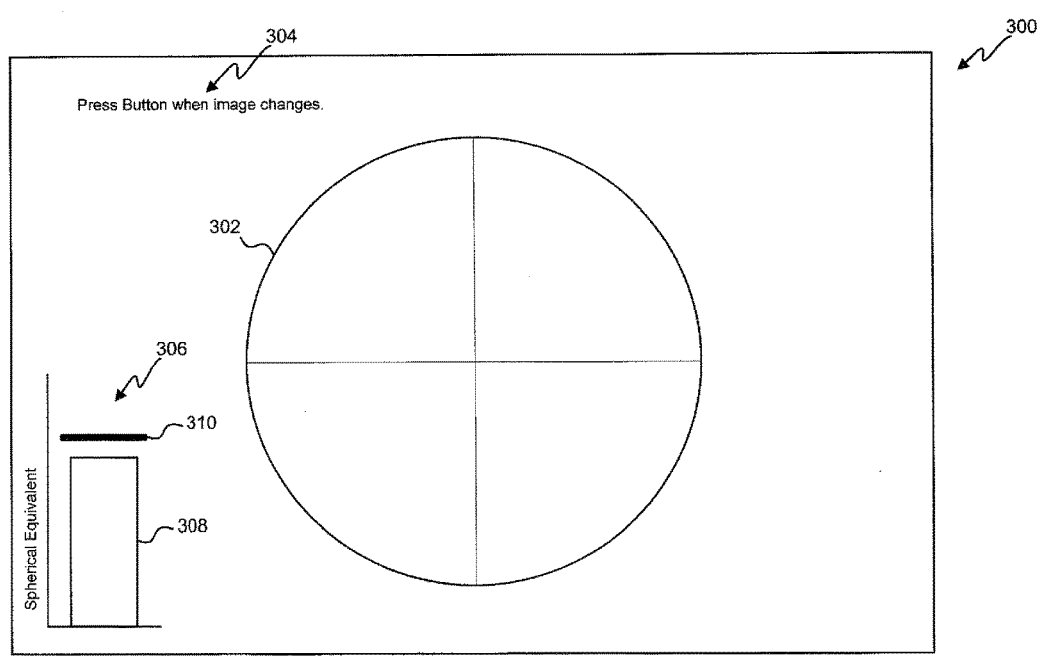
FIG. 3 is a schematic illustration of one embodiment of the patient interface of the wavefront interactive refractor.

With reference now to FIG. 3 a schematic illustration of one embodiment of the patient visual display 300 of the wavefront interactive refractor 112 is shown. The patient visual display 300 can, as discussed above be provided by the patient interface engine 204, and particularly by the patient output device 122. The patient visual display 300 can comprise a target 302. The target can be an image or object. In some embodiments, the target can be manipulated and/or changed to facilitate changes in the, date of state of the patient's eye 102 and/or to facilitate the relaxation of the patient and the fully relaxed state of the patient's eye 102. In one embodiment, for example, the target 302 can be displayed to the patient in focus, and then can be moved to an out of focus, fogged position. In some embodiments, the speed and/or the amount of motion of to target 302 can be controlled by the user to affect a change in the refractive state of the patient's eye 102.

The target can be changed in a variety of ways to stimulate relaxation of the eye 102 and to facilitate in generating data relating to the refractive state of the eye 102. In some embodiments, the target 302 can be moved laterally with respect to the patient's eye 102 and in some embodiments, the target 302 can be moved relatively closer to and/or relatively further from the patient's eye 102. In some embodiments, the visual distance to the target 302 can be changed. This can be accomplished by manipulating the wavefront of the target 302 from a first wavefront to a second wavefront, which first wavefront mimics the wavefront of an object located at a first distance from the patient's eye 102 and the second wavefront mimics the wavefront of an object located at a second distance from the patient's eye 102.

In some embodiments, the target 302 can be adjustable so as to have a different size, shape, and/or color. In some embodiments, the brightness, contrast, and/or focus of the target 302 can be changed. In some embodiments, the target 302 can be changed from a first image to a second, and in some embodiments, the image of the target 302 can be changed as many times as desired.

The target 302 can be any desired image and/or object and/or any desired type of image and/or type of object. In some embodiments, the target 302 can comprise a point of light having any desired shape. In some embodiments, the target 302 can comprise, for example, a crosshair as depicted in FIG. 3, a landscape, a string, video images, an animation, or any other image. In some embodiments, the target type may be varied to facilitate relaxation of the accommodation of the eye 102 and to facilitate the generation of data relating to the refractive state of the eye 102. In some embodiments, for example, the manipulation and/or change of the target 302 can relate to the patient task.

As seen in FIG. 3, the patient visual display 300 comprises a task indicator 304. In some embodiments, the task indicator 304 can provide the patient information relating to past, current, and/or future tasks. In some embodiments, the task indicator 304 can provide the instruction telling the patient how to perform the task. As seen in FIG. 3, the task indicator 304 can comprise a text string.

Patient visual display 300 can, in some embodiments, provide an indicator 306 of the refractive state of the patient's eye 102. In some embodiments, for example, the indicator 306 of the refractive state of the patient's eye 102 can provide an indication of the absolute refractive state of the patient's eye 102 and/or of the relative refractive state of the patient's eye 102. In some embodiments, for example, the indicator 306 of the refractive state of the patient's eye 102 can provide information regarding the refractive state of the patient's eye 102 versus time, the refractive state of the patient's eye 102 versus task, the refractive state of the patient's eye 102 versus pupil size, and/or the refradctive state of the patient's eye 102 versus any other desired and changing parameter.

In some embodiments, the indicator 306 can further comprise an indicator of the size of the pupil of the patient's eye 102 that can be separate from the indicator 306 of the refractive state of the patient's eye 102 and/or integral in the indicator 306 of the refractive state of the patient's eye 102. In some embodiments, for example, this indicator of the pupil size can comprise a plot of pupil size versus time, and in some embodiments, the indicator of the pupil size can comprise a color scheme of the indicator 306 of the refractive state of the patient's eye 102. Thus, in some embodiments, the indicator 306 of the refractive state of the patient's eye 102 can comprise a first color when the pupil is an undesireable size, and a second color when the pupil is a desireable color. In some embodiments, for example, the color scheme can further comprise a third color indicative of the occurrence of a desired change in the pupil size, and a fourth color indicative of the occurrence of an undesired change in the pupil size.

In the embodiment depicted in FIG. 3, the indicator 306 of the refractive state of the patient's eye 102 comprises a status indicator 308 and a goal indicator 310. The status indicator 308 can provide the current refractive state of the patient's eye 102. In some embodiments, for example, the current refractive state of the patient's eye 102 includes the refractive state of the patient's eye 102 measured with in the past 200 ms, past 100 ms, the past 50 ms, the past 30 ms, and/or the past 10 ms. In some embodiments, for example, the current refractive state of the patient's eye 102 can include the refractive state of the patient's eye 102 as measured in between the past 200 ms and the past 30 ms.

The fluctuations in the focus of the eye are known to be divided into two different frequency regimes. These are the low frequency component (LFC) and the high frequency component (HFC). The low frequency component occurs at rates of about 5 hertz or slower and can be thought of as being the change in focus that occurs when a person is observing a visual field under conscious control or awareness. The low frequency changes can vary from far to near focus through the entire range of focus that the eye can achieve. The high frequency component occurs at a faster rate of about 10 hertz or faster and it is associated with small changes in focus. This is also sometimes called focus tremor. The focus tremor is automatic and unconscious. It is thought that these micro-fluctuations are used by the eye to assist the nervous system in achieving a desired focus on a target. It has been reported in the literature that when the eye has approached the extreme ends of its focus range, either the most near or the most far focus, that the amplitude of the HFC becomes diminished. Thus a reduction in HFC can be seen as an indicator of when an eye has reached its most fully relaxed state. So it would be useful for a doctor to be able to view an indicator showing the strength of the HFC. The speed of the HFC can exceed the rate at which a standard computer software will update a display. So it would be beneficial for the software to collect and analyze high speed data, taken for instance at 30 hertz, and then display at a slower rate an indication of the amplitude of the micro fluctuations during a prescribed time period, for instance over 0.2 seconds. Such an metric may simply be the difference between the maximum and minimum values of the spherical equivalent seen during the time period. More sophisticated metrics, such as a root mean square value may be useful as well, In some embodiments of the wavefront interactive refractor 112, the status indicator 308 can be continually updated to reflect the current refractive state of the patient's eye 102 during the time period in which the scanning engine 208 collects data relating to the refractive state of the patient's eye 102. Thus, the status indicator 308 can, during operation of the scanning engine 208, continually adjust upward down as the refractive state of the patient's eye 102 changes. In one particular embodiment, for example, a more hyperopic refraction can result in the status indicator 308 becoming taller and/or larger, and a less hyperopic refraction can result in the status indicator 308 becoming shorter and/or smaller. In some embodiments, the status indicator 308 can indicate and/or identify a time for capturing data indicating the refractive state of the patient's eye 102 when the status indicator 308 reaches and/or surpasses the goal indicator 310.

The goal indicator 310 can comprise a visual indication of a minimum desired refractive state to be achieved before capturing the refractive state of the eye 102. In some embodiments, the goal indicator 310 can be a specific goal indicator, and in some embodiments, the goal indicator 310 can be a general goal indicator. In embodiments in which the goal indicator 310 is a general goal indicator, the goal indicator can represent a value that is nonspecific to the patient and can, for example, represent an average refractive state of eyes in a population that can, for example, the defined by age, gender, race, health, or any other desired parameter. In some embodiments, the goal indicator 310 can comprise a threshold value associated with the treatment procedure. In some embodiments in which the goal indicator 310 is a specific goal parameter, the goal indicator 310 can be generated based on an aspect of the patient data. In some embodiments, this can include the most desirable refractive state of the patient's eye exhibited over the course of evaluation of the patient's eye 102 with the wavefront interactive refractor 112, the refractive state of the patient's eye 102 that was measured during another and/or previous test such as, the manifest refraction, and/or the refractive state of the patient's eye 102 that was collected during the performance of a specific task. The goal indicator 310 can comprise any feature and/or image that allows the patient and/or user to ascertain whether the current refractive state of the patient's eye 102 is more or less desirable than the threshold and/or level indicated by the goal indicator 310.

Figure 4:
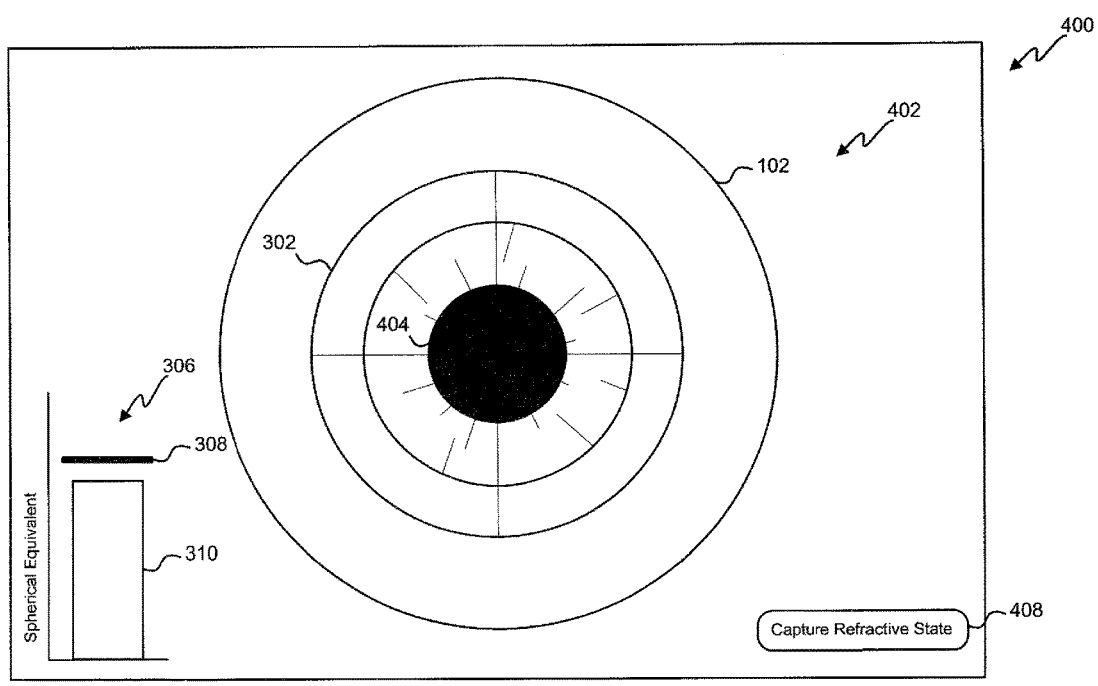
FIG. 4 is a schematic illustration of one embodiment of the user interface of the wavefront interactive refractor.

With reference now to FIG. 4, a schematic illustration of one embodiment of the user visual display 400 of the wavefront interactive refractor 112 is shown. The user visual display 400 can provide information in visual format to the user of the wavefront interactive refractor 112. In some embodiments, the user visual display 400 can comprise a component of the user interface 202.

As seen in FIG. 4, the user visual display 400 comprises an alignment indicator 402. In some embodiments, for example, the alignment indicator 402 can be configured to facilitate in aligning patient's eye 102 with the wavefront interactive refractor 112. In some embodiments, for example, the alignment indicator 402 can be configured to display an image of the patient's eye 112 and an indicator of the alignment of the patient's eye 112 relative to the wavefront interactive refractor 112 and/or the target 302. In some embodiments, for example, the alignment indicator 402 can display the target 302 overlaid on top of the patient's eye 112 to thereby allow patient's eye 112 to be positioned in the desired alignment with respect to the wavefront interactive refractor 112. As seen in FIG. 4, in one embodiment, the patient's eye 102 can be aligned with the wavefront interactive refractor 112 so that the target is centered over the pupil 404 of the patient's eye 102.

As also seen in FIG. 4, the user visual display 400 can comprise a indicator 306 of the refractive status of the patient's eye 102 including, the status indicator 308 and the goal indicator 310. In some embodiments, and as seen in FIG. 4, the indicator 306 can display changes to the refractive state of the patient's eye 102 in terms of spherical equivalent of the patient's eye 102.

In some embodiments, the user visual display 400 can comprise a button 408 that allows the user to provide to request the capture of the refractive state of the patient's eye 102. In some embodiments, the button 408 can be a selectable icon located within the user visual display 400, and in some embodiments, the button 408 can comprise any other feature configured to provide an input to the wavefront interactive refractor 112. In some embodiments, a feature of the button can change to identify a time for capturing refractive state data for the patient's eye 102. In some embodiments, for example, these changes can include a change in the size, color, shape, illumination, and/or appearance of the button 408. In some embodiments, for example, the button can be a first color, such as, for example, yellow when refractive state data is first collected, which color can indicate that there is insufficient data to provide trend information relating to the refractive state of the eye 102. In some embodiments, a desired trend in the refractive state data can be indicated by a second color, such as, for example, green, of the button 408, and an undesired trend in the refractive state data can be indicated by a third color such as, for example, red, of the button 408.

With reference now to FIGS. 5A-5D, different embodiments of the indicator 306 are shown. Although the indicators 306 depicted in FIGS. 5A-5D comprise visual indicators, in some embodiments, the indicator 306 can comprise a non-visual indicator such as, for example, an audible signal comprising a changing tone, pitch, and/or volume based on the refractive state of the patient's eye 102 and/or the size of the pupil of the patient's eye.

As seen in FIG. 5A, the indicator 306-A comprises a radial type indicator. The indicator 306-A includes a status indicator 308-A that radially extends from the center of the indicator 306-A. The indicator 306-A further includes a goal indicator 310-A located a distance from the zero indicator 500. In the embodiment depicted in FIG. 5A, the status indicator 308-A is located between the zero indicator 500 and the goal indicator 310-A, thereby indicating that the threshold of the goal indicator 310-A is not currently reached.

With reference now to FIG. 5B, a color indicator 306-B is shown. In the embodiment shown in FIG. 5B, the color indicator 306-B includes the pupil size indicator 502 and refractive state indicator 504. In some embodiments, for example, the size of the pupil can be an important consideration in determining the refractive state of the eye 102 and determining whether the patient is suited for certain treatment procedures. Thus, in some embodiments it can be advantageous to include an indicator of the pupil size in the user visual display 400. In such an embodiment, the measured pupil size of the patient's eye can be compared to the threshold pupil size demarking between acceptable sizes and unacceptable sizes. In some embodiments in which the pupil size is acceptable, the pupil indicator 502 can display a first color indicative of the acceptability of the pupil size. In contrast, if the pupil size is unacceptable, the people indicator 502 can display a second color indicative of the acceptability of the pupil size. Similarly, in some embodiments if the pupil size changes to become more acceptable and/or closer to being acceptable, the pupil indicator 502 can display a first color and if the pupil size changes so that the pupil is less acceptably sized, the pupil indicator 502 can display a second color. In some embodiments, for example, the pupil size can be acceptable when the pupil is less than or equal to 6 mm, and the pupil size can be unacceptable when the pupil is greater than or equal to 6 mm.

The embodiment depicted in FIG. 5B further includes a status indicator 308-B. In some embodiments, the status indicator 308-B of the indicator 306-B can provide a color based visual signal of the direction of change and/or acceptability of the refractive status of the patient's eye 102. Thus, in some embodiments, the status indicator 308-B can display a first color when the refractive state of the patient's eye 102 is desirable and/or is becoming more desirable, and the status indicator 308-B can display a second color when the refractive state of the patient's eye 102 is undesirable and/or is becoming more undesirable. In some embodiments, the color scheme comprising multiple colors can be used to indicate the different degrees of desireability and/or undesirable of the refractive state of the patient's eye 102.

FIG. 5C depicts one embodiment of an indicator 306-C in which the refractive status of the eye 102 is plotted as a function of time. In some embodiments, the refractive status of the eye 102 can be plotted as a function of, for example, task target characteristic, or diagnosis activity. This format of the indicator 306-C advantageously allows the user and/or the patient to view trends in the refractive status of the patient's eye 102 and/or identify tasks and/or situations resulting in a more desirable refractive state of the patient's eye 102. As seen in FIG. 5C, the indicator 306-C includes the status indicator 308-C and the goal indicator 310-C. In some embodiments, the wavefront interactive refractor 112 can calculate turning points in the data represented by the status indicator 308-C, which turning points can be used to better identify activities and/or events causing a positive effect on the refractive status of the eye 102 and activities and/or events causing a negative effect on the refractive status of the eye 102.

FIG. 5D depicts one embodiment of an indicator 306-D, which indicator 306-D is similar to the indicator 306 discussed in connection with FIGS. 3 and 4 above. As discussed in those figures, the indicator 306-D includes status indicator 308-D the that moves up and down as the status of the eye 102 changes, and the goal indicator 310-D that allows determination of whether the refractive status of the eye 102 has reached the desired goal status or the eye 102.

Figure 6:
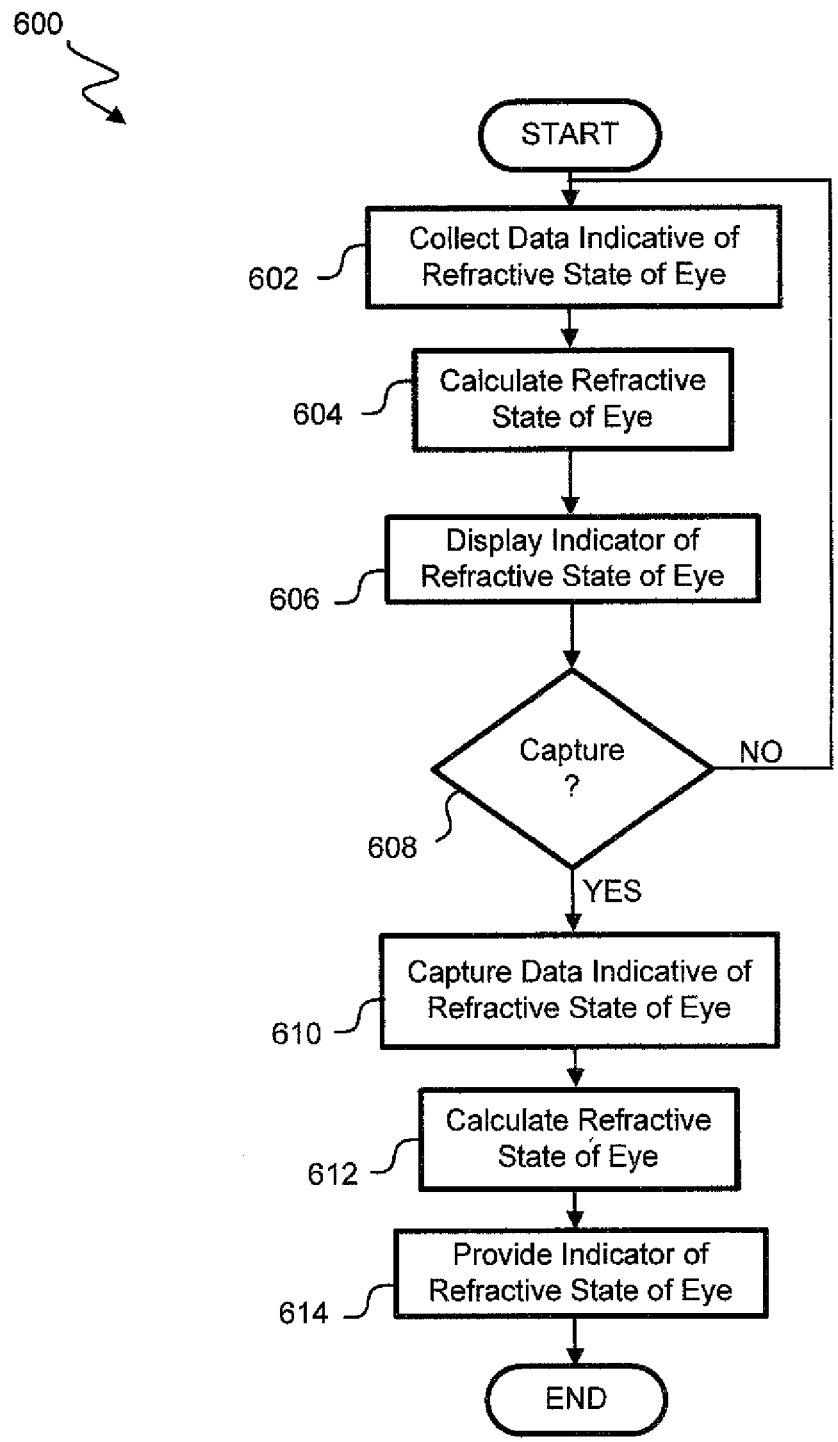
FIG. 6 is a flowchart illustrating one embodiment of a process for identifying a time for capturing the refractive state of an eye.

With reference now to FIG. 6, a flowchart illustrating one embodiment of a process 600 for identifying a time for capturing the refractive state of an eye 102 is shown. The process 600 can be performed by the wavefront interactive refractor 112, and/or a component of the wavefront interactive refractor 112. The process 600 involves the collection of data indicative of a refractive state of the eye, the calculation of the refractive state of the eye 102 using the collected data, and displaying an indicator of the refractive state of the eye 102, and, if it is determined to capture data indicative of the refractive state of the eye 102, capturing data indicative of the ice refractive state. The process 600 begins at block 602 wherein the data indicative of the refractive state of the eye 102 is collected. In some embodiments, for example, this data can be collected by the scanning engine 208. In some embodiments, this data indicative of the refractive suit the patient's eye 102 can be collected by measuring a wavefront of light passing through the patient's eye 102. The details of how this wavefront of light can be generated are discussed at greater length above with respect to FIG. 1.

After the data indicative of the refractive state of the eye 102 is collected, the process 600 proceeds to block 604 wherein the refractive state of the eye 102 is calculated. In some embodiments, for example, the calculation the refractive state of the eye 102 can include processing the data indicative of the refractive state of the eye 102 with a component of the wavefront interactive refractor 112 such as, for example, the processor 200. In some embodiments, for example, this calculation can be based on a full wavefront reconstruction, and in some embodiments this calculation can be performed using the Zernike slope dot-product, which can provide the sphere, cylinder, and axis of the patient's eye 102.

After the refractive state of the eye 102 is calculated, the process 600 proceeds to block 606 wherein an indicator of the refractive state of the eye 102 is displayed. In some embodiments, for example, this indicator of the refractive state of the eye 102 can comprise the indicator 306 discussed at greater length in FIGS. 3, 4, 5 above. In some embodiments, the indicator 306 can be displayed to the user and/or patient.

After the indicator of the refractive state of the eye is displayed, the process 600 proceeds to decision state 608 wherein it is determined whether to capture data indicative of the refractive state of the eye 102. In some embodiments, for example, the capture of data indicative of the refractive state of the eye 102 can differ from the collection of data indicative of the refractive state of the eye 102 in that the capture data can comprise a definitive measure of the refractive state of the patient's eye 102. In some additional embodiments, the captured data indicative of the refractive state of the eye 102 can differ from the collected data indicative of the refractive to the eye 102 in that the captured data indicative of the refractive state of the eye 102 is stored.

In some embodiments, the wavefront interactive refractor 112 can receive an indication from the user and/or patient to capture data indicative of the refractive state of the eye. In some embodiments, for example, this indication can be provided to the wavefront interactive refractor with button 408 or any other feature of the user interface 202 and/or patient interface 204 configured to initiate capture of the refractive state of the patient's eye 102. If it is determined not to capture data indicative of the refractive student the eye 102, then the process 600 can return to block 602 and continue the collection of data indicative of the refractive state of the eye.

If it is determined to capture data indicative of the refractive state of the eye 102, then the process 600 proceeds to block 610 wherein data indicative of the refractive state of the eye 102 is captured. In some embodiments, this capture can proceed in the same manner as outlined above with respect to block 602.

In some embodiments, data indicative of the refractive state of the eye 102 can be captured immediately after it is determined to capture data relating to the refractive state of the eye 102, and in some embodiments, a set of data before and/or after it is determined to capture data relating to the refractive state of the eye 102 can be captured. In some embodiments, this data can include the refractive state of the patient's eye 0.5 seconds, 1 second, 2 seconds, 3 seconds, 4 seconds, 5 seconds, 10 seconds, and/or any other or intermediate time before and/or after it is determined whether to capture data relating to the refractive state of the eye 102. In some embodiments, this data can be analyzed to determine the most desired refractive state of the eye 102 in the captured data.

In some embodiments, in contrast to the collection of data indicative of the refractive state of the eye 102, the scanning engine 208 can be configured to operate at a higher resolution and/or with greater accuracy when capturing data indicative of the refractive state of the eye 102 than when collecting data indicative of the refractive state of the eye as discussed to block 602. In some embodiments, for example, the lower resolution of the data gathered by the scanning engine 208 during the collection of data indicative of the refractive state of the eye 102 can facilitate accelerating the calculation of the refractive state of the eye to thereby more quickly update the indicator 306 with data reflecting the current refractive state of the eye 102.

In some embodiments, the data indicative of the refractive state of the eye 102 captured in block 610 can be stored in the memory 210 of the wavefront interactive refractor 112 including, for example, in the scan database 214 of the memory 210 of the wavefront interactive refractor 112. In some embodiments, for example, this captured data can be associated with the patient, the patient's eye, the user, the time and/or date that the data was captured, and/or any other desired information.

After the data indicative of the refractive state of the eye is captured, the process 600 proceeds to block 612 wherein the refractive state of the eye 102 is calculated. In some embodiments, this calculation can be performed in the same manner as described with respect to block 604, but in embodiments in which the resolution and/or accuracy of the captured data indicative of the refractive state of the eye is greater than the resolution and/or accuracy of the collected data indicative of the refractive state of the eye 102, this calculation can likewise provide more accurate and better resolution in the calculation results.

In some embodiments, for example, the calculation the refractive state of the eye can include processing the data indicative of the refractive state of the eye with a component of the wavefront interactive refractor 112 such as, for example, the processor 200. In some embodiments, for example, this calculation can be based on a full wavefront reconstruction, and in some embodiments this calculation can be performed using the Zernike slope dot-product, which can provide the sphere, cylinder, and axis of the patient's eye 102. Is calculated refractive the state of the eye can be stored in the memory 210 of the wavefront interactive refractor 112 including, for example, in the scan database 214 of the memory 210 of the wavefront interactive refractor 112. In some embodiments, for example, this capture data can be associated with the patient, the patient's eye, the user, the time and/or date that the data was captured, and/or any other desired information.

After the refractive state of the eye 102 is calculated, the process proceeds to block 614 wherein an indicator of the refractive state of the eye 102 is provided. In some embodiments this indicator can be provided via the user and/or patient interface 202, 204 or via the communication engine 206 to another device.

Figure 7:
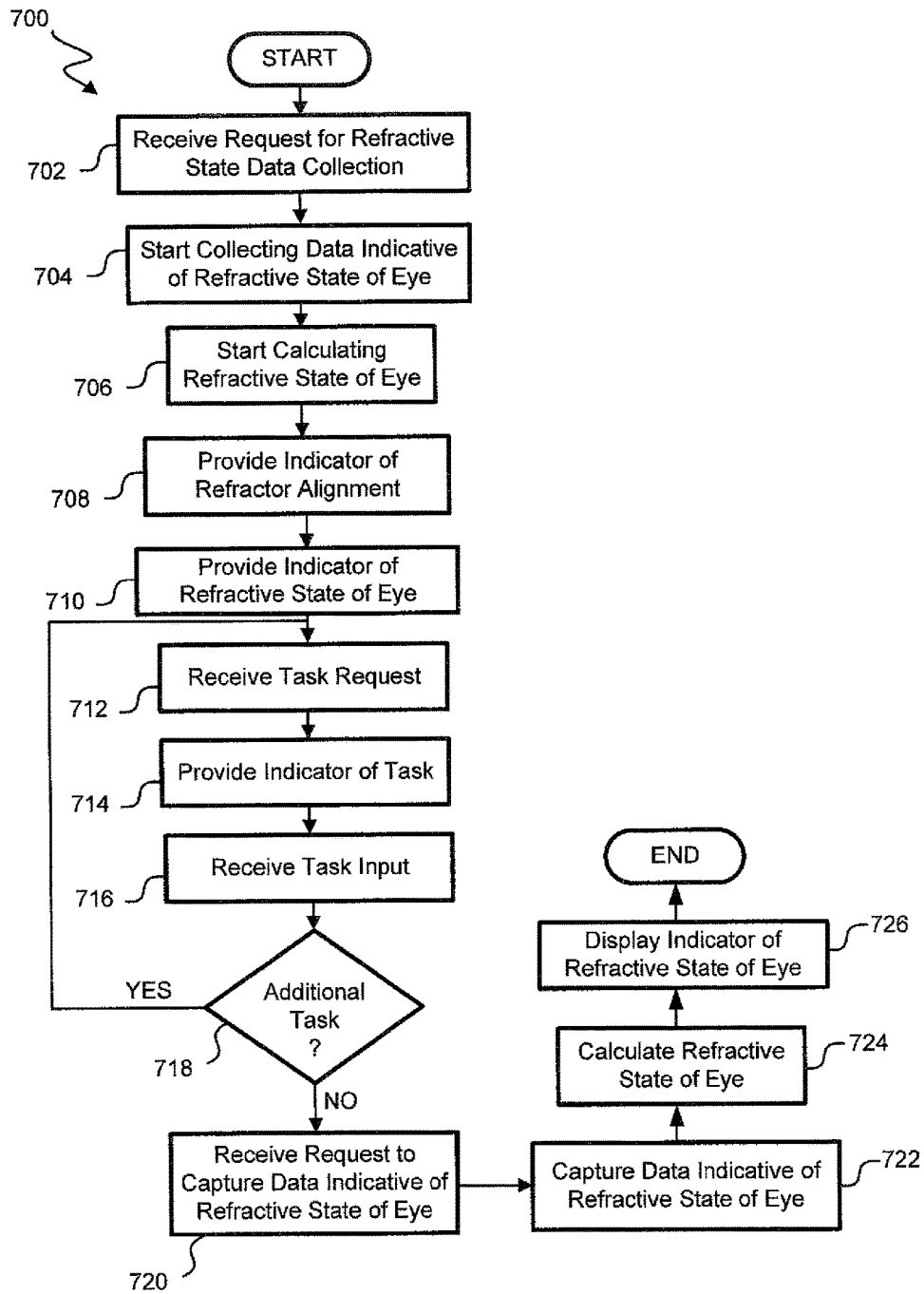
FIG. 7 is a flowchart illustrating another embodiment of a process for identifying a time for capturing the refractive state of an eye.

With reference now to FIG. 7, flowchart illustrating another embodiment of a process for identifying a time for capturing the refractive state of an eye is shown. The process 700 can be performed by the wavefront interactive refractor 112, and/or a component of the wavefront interactive refractor 112. The process 700 involves the collection of data indicative of a refractive state of the eye, and using that data to calculate the refractive state of the patient's eye 102, to provide an indicator of the refractive state of the patient's eye 102, and to identify a time at which to capture data indicative of the refractive state of the patient's eye 102. The process 700 begins at block 702 wherein a request for refractive state data collection is received. In some embodiments, for example, this request can be provided by a patient and/or user and can be received by the user interface 202, the patient interface 204, and/or the communication engine 206.

After the request for refractive state data collection has been received, the process 700 proceeds to block 704 wherein the collecting of data indicative of the refractive state of the eye 102 is started. In some embodiments, for example, the collection of data indicative of the refractive state of the eye 102 can be continuously performed until the process 700 terminates and/or until an input is received requesting the ending of the collection of that data.

In some embodiments, for example, this data can be collected by the scanning engine 208. In some embodiments, this data indicative of the refractive state of the patient's eye 102 can be collected by measuring a wavefront of light passing through the patient's eye 102. The details of how this wavefront of light can be generated are discussed at greater length above with respect to FIG. 1.

After the collecting of data indicative of the refractive state of the eye 102 is started, the process 700 proceeds to block 706 wherein the calculation of the refractive state of the eye 102 is started. In embodiments in which data indicative of the refractive state of the eye 102 is continuously and/or repeatedly collected, the refractive state of the eye 102 can likewise be continuously and/or repeatedly calculated. Advantageously, this continuous and/or repeated calculation of the refractive state of the eye 102 can allow display of more accurate information relating to the current refractive state of the eye 102.

In some embodiments, for example, the calculation of the refractive state of the eye 102 can include processing the data indicative of the refractive state of the eye with a component of the wavefront interactive refractor 112 such as, for example, the processor 200. In some embodiments, for example, this calculation can be based on a full wavefront reconstruction, and in some embodiments this calculation can be performed using the Zernike slope dot-product, which can provide the sphere, cylinder, and axis of the patient's eye 102.

After the calculating of the refractive state of the eye 102 is started, the process 700 proceeds to block 708 wherein an indicator of the wavefront interactive refractor alignment is provided. In some embodiments, for example, this indicator of the wavefront interactive refractor alignment can comprise the alignment indicator 402 depicted in FIG. 4. In some embodiments, the indicator of the alignment of the wavefront interactive refractor 112 can facilitate in determining whether the patient's eye 102 is properly aligned so as to allow generation of accurate data reflecting the refractive state of the patient's eye 102. In some embodiments, the wavefront interactive refractor 112 can comprise features configured to allow the patient and/or user to affect the alignment of the eye 102 relative to the wavefront interactive refractor 112. In some embodiments, for example, these features can allow the repositioning of the eye 102 relative to the wavefront interactive refractor 112 so as to properly aligned the eye 102. In some embodiments, for example, the alignment of the eye 102 with respect to the wavefront interactive refractor 112 can result in the relaxation of the accommodation of the eye 102, which relaxation can influence the refractive state of the eye. In some embodiments, any change in the accommodative state of the eye 102 occurring during the alignment of the wavefront interactive refractor 112 with eye 102 can be indicated in the collected data indicative of the refractive state of the eye 102. In some embodiments, for example, aspects of the aligning of the wavefront interactive refractor 112 with the eye 102 can be manipulated to affect a desired change in the refractive state of the eye. Thus, in some embodiments, aspects of the aligning of the wavefront interactive refractor 112 with the eye 102 can be performed for the purpose of determining their effect on the refractive state of the eye 102, and in some embodiments, can be performed for the purpose of creating an capturing a desired refractive state of the eye 102.

After the indicator of the alignment of the wavefront interactive refractor 112 has been provided, the process 700 proceeds to block 710 wherein an indicator of the refractive state of the eye 102 is provided. In some embodiments, for example, this indicator of the refractive state of the eye 102 can comprise the indicator 306 discussed at greater length in FIGS. 3, 4, 5 above. In some embodiments, the indicator 306 can be displayed to the user and/or patient. In some embodiments, the this indicator 306 can be updated as new calculations of the refractive state of the patient's eye 102 are completed and/or performed. In some embodiments, for example, the indicator of the refractive state of the eye 102 can be continuously provided during process 700 so as to provide information on any changes in the refractive state of the eye 102.

After an indicator of the refractive state of the eye 102 is provided, the process proceeds to block 712 wherein a task request is received. In some embodiments, for example, the patient and/or user can request a task to facilitate the achievement of the desired refractive state of the eye 102. In some embodiments, this task can be configured to provide the patient with a distraction so as to encourage relaxation of the accommodation of the eye 102. In some embodiments, the task request can be received by the user interface 202, the patient interface 204, and/or the communication engine 206.

After the task request is received, the process 700 proceeds to block 714 wherein an indicator of the task is provided. In some embodiments, for example, the indicator of the task can comprise a task indicator 304 discussed at length above. In some embodiments, the indicator of the task can be configured to provide information to the patient and/or user relating to the task and how to complete the task. In some embodiments, the indicator of the task can be displayed to the patient via the patient visual display 300 and/or to the user via the user visual display 400.

After the indicator of the task is provided, the process 700 proceeds to block 716 wherein a task input is received. In some embodiments, the task input can comprise an indicator of the performance and/or completion of the task by the patient and/or user. In some embodiments, for example, the task input can be provided to the wavefront interactive refractor 112 via, for example, the user interface 202 and/or the patient interface 204. In some embodiments, for example, the task input can be provided by the patient input device 124.

After the task input has been received, the process proceeds to decision state 718 wherein it is determined if there is an additional task. In some embodiments, this determination can include querying the task database 212 to determine whether all of the tasks have been provided to the patient and/or user. If it is determined that there are additional tasks, then the process can return to block 712. If it is determined that there are no additional tasks, or at any other point in process 700, the wavefront interactive refractor 112 can receive a request to capture data indicative of the refractive state of the eye 102. This request can be provided by the patient and/or user to the wavefront interactive refractor 112 via the user interface 202, the patient interface 204, and/or the communication engine 206.

After the request to capture data indicative of the refractive state of the eye 102 is received, the process 700 proceeds to block 722 wherein data indicative of the refractive state of the eye 102 is captured. In some embodiments, this capture can proceed in the same manner as outlined above with respect to block 704. In some embodiments, in contrast to the collection of data indicative of the refractive state of the eye 102, the scanning engine 208 can be configured to operate at a higher resolution and/or with greater accuracy when capturing data indicative of the refractive state of the eye 102 than when collecting data indicative of the refractive state of the eye 102 as discussed in block 704. In some embodiments, for example, the lower resolution of the data gathered by the scanning engine 208 during the collection of data indicative of the refractive state of the eye 102 can facilitate decreasing the time required for the calculation of the refractive state of the eye 102 which can thereby allow faster updates of the indicator 306 with data reflecting the current refractive state of the eye 102.

In some embodiments, the data indicative of the refractive state of the eye 102 captured in block 722 can be stored in the memory 210 of the wavefront interactive refractor 112 including, for example, in the scan database 214 of the memory 210 of the wavefront interactive refractor 112. In some embodiments, for example, this captured data can be associated with the patient, the patient's eye 102, the user, the time and/or date that the data was captured, and/or any other desired information.

After the data indicative of the refractive state of the eye 102 is captured, the process 700 proceeds to block 724 wherein the refractive state of the eye 102 is calculated. In some embodiments, this calculation can be performed in the same manner as described with respect to block 706, but in embodiments in which the resolution and/or accuracy of the captured data indicative of the refractive state of the eye 102 is greater than the resolution and/or accuracy of the collected data indicative of the refractive state of the eye 102, this calculation can likewise provide more accurate and better resolution in the calculation results.

In some embodiments, for example, the calculation the refractive state of the eye can include processing the data indicative of the refractive state of the eye with a component of the wavefront interactive refractor 112 such as, for example, the processor 200. In some embodiments, for example, this calculation can be based on a full wavefront reconstruction, and in some embodiments this calculation can be performed using the Zernike slope dot-product, which can provide the sphere, cylinder, and axis of the patient's eye 102. Is calculated refractive the state of the eye can be stored in the memory 210 of the wavefront interactive refractor 112 including, for example, in the scan database 214 of the memory 210 of the wavefront interactive refractor 112. In some embodiments, for example, this captured data can be associated with the patient, the patient's eye 102, the user, the time and/or date that the data was captured, and/or any other desired information.

After the refractive state of the eye 102 is calculated, the process 700 proceeds to block 726 wherein an indicator of the refractive state of the eye 102 is provided. In some embodiments this indicator can be provided via the user and/or patient interface 202, 204 or via the communication engine 206 to another device.

Figure 8:
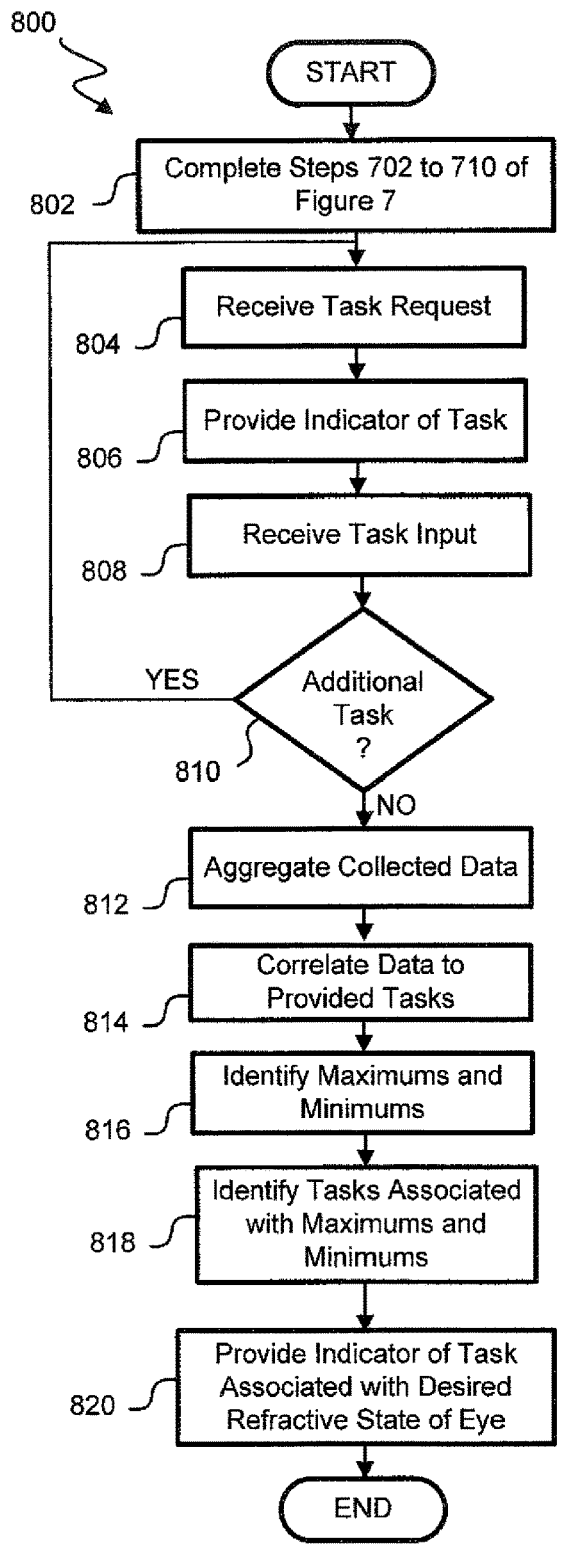
FIG. 8 is a flowchart illustrating one embodiment of a process for identifying a patient task resulting in a desired refractive state of an eye.

With reference now to FIG. 8, a flowchart illustrating one embodiment of a process 800 for identifying a patient task resulting in a desired refractive state of the eye 102 is shown. In some embodiments, and as discussed above, the performance of different tasks by the patient can result in different refractive states of the patient's eye 102. In some embodiments, some or all of these refractive states may achieve desired levels, and in some embodiments, some or all of these refractive states may not achieve desired levels. Thus, the determination of the task associated with an achieved refractive state of the eye 102 can advantageously allow the performance of the task resulting in a desired refractive state of the eye, and capturing data relating to this refractive state of the eye 102.

The process 800 begins at block 802 wherein the steps discussed in blocks 702 through 710 of FIG. 7 are performed. After the steps discussed in blocks 702 through 710 of FIG. 7 have been performed, the process 800 proceeds to block 804 wherein a task request is received. In some embodiments, for example, the patient and/or user can request a task to facilitate the achievement of the desired refractive state of the eye 102. In some embodiments, this task can be configured to provide the patient with the distraction so as to encourage relaxation of the accommodation of the eye. In some embodiments, the task request can be received by the user interface 202, the patient interface 204, and/or the communication engine 206.

After the task request is received, the process 800 proceeds to block 806 wherein an indicator of the task is provided. In some embodiments, for example, the indicator of the task can comprise a task indicator 304 discussed at length above. In some embodiments, the indicator of the task can be configured to provide information to the patient and/or user relating to the task and how to complete the task. In some embodiments, the indicator of the task can be displayed to the patient via the patient visual display 300 and/or to the user via the user visual display 400.

After the indicator of the task is provided, the process 800 proceeds to block 808 wherein a task input is received. In some embodiments, the task input can comprise an indicator of the performance and/or completion of the task by the patient and/or user. In some embodiments, for example, the task input can be provided to the wavefront interactive refractor 112 via, for example, the user interface 202 and/or the patient interface 204. In some embodiments, for example, the task input can be provided by the patient input device 124.

After the task input has been received, the process 800 proceeds to decision state 810 wherein it is determined if there is an additional task. In some embodiments, this determination can include querying the test database 212 to determine whether all of the tasks have been provided to the patient and/or user. If it is determined that there are additional tasks, then the process can return to block 804.

If it is determined that there are no additional task, then the process 800 can proceed to block 812 and aggregate the collected data indicative of the refractive state of the eye 102. In some embodiments, for example, the aggregation of the collected data indicative of the refractive state of the eye 102 can include ending the collection of data indicative of the refractive state the eye 102, and in some embodiments the collection of data indicative of the refractive state of the eye 102 can continue during the aggregation of the collected data indicative of the refractive state of the eye 102. In some embodiments, for example, in which the collection of data continues after the aggregation of the collected data is started, the aggregation can be, for example, limited to data collected before the start of the aggregation, and in some embodiments, the aggregation may not be limited to any data set, but may rather update as additional data is received.

In some embodiments, the aggregation of the collected data can be performed by a component of the wavefront interactive refractor 112 such as, for example, the processor 200 and/or the memory to 10 including the test database 212 and/or the scan database 214. In some embodiments, for example, collected data indicative of the refractive state of the eye 102 can be retrieved from the memory 210 including, for example, the test database 212 and/or the scan database 214.

After the collected data has been aggregated the process 800 proceeds to block 814 wherein provided task are correlated with the collected data. In some embodiments, this correlation can include providing an indicator in the time sequence of the refractive state of the patient's eye as to the perform task was started and/or when the perform task was completed. In some embodiments, this correlation of the provided tasks with the collected data can further include correlating any detected action performed using the wavefront interactive refractor 112 with the time sequence of the refractive state of the patient's eye 102. This can include, for example, any change to the alignment of the eye 102 with respect to the wavefront interactive refractor 112 and/or any non-task related change to the target 302 and/or to the patient visual display 300.

After the tasks are correlated to the data, the process 800 proceeds to block 816 wherein maximums and minimums in the aggregated data indicative of the refractive state of the eye 102 are identified. In some embodiments, for example, the identification of the one or several maximums and/or minimums can be performed by a component of the wavefront interactive refractor 112 including, for example, the processor 200.

After the minimums and/or maximums in the aggregated data indicative of the refractive state of the eye 102 are identified, the process 800 proceeds to block 818 wherein tasks associated with the minimums and maximums identified. In some embodiments, for example, this can include determining the task associated with the time in which a minimum and/or maximum was achieved and/or determining the task that is temporally most proximate to the time at which a minimum and/or maximum was achieved.

In some embodiments, for example, the calculated minimums and/or maximums associated with the aggregated data indicative of the refractive state of the patient's eye 102 can be compared against the desired refractive state of the patient's eye 102.

After the tasks associated with the minimums and/or maximums identified, the process proceeds to block 820 wherein an indicator of one or several tasks associated with the desired refractive state of the eye 102 is provided. In some embodiments, for example, the identified minimums and/or maximums can be compared to the desired refractive state of the eye 102. This comparison can allow the identification of tasks resulting in a refractive state of the eye 102 that is most desired, meets the desired refractive state of the eye 102, and/or comes closest to meeting the desired refractive state of the eye 102. In some embodiments, this information can be provided to the user and/or patient via, for example, via a component of the user interface 202 such as, for example, the user visual display 400 and/or via a component of the patient interface 204 such as, for example, the patient visual display 300.

In some embodiments, after the tasks associated with minimums and/or maximums identified, this information can be provided to the test database 212. This information can be used to create a task list in the task database 212, which task list is specific to the patient and can be used to facilitate the identification of a time for capturing eye refraction data, and/or for capturing eye refraction data when the eye is in a desired refractive state. In such an embodiment, the process 800 can proceed to block 712 of FIG. 7.

With reference now to FIG. 9, a list 900 of tasks is provided. In some embodiments, and as discussed at greater length above, a task can be provided to the patient to facilitate in identifying a time for capturing refractive state data of the eye 102, and to facilitate achieving a desired refractive state of the eye. In some embodiments, these tasks can include, gripping a portion of the wavefront interactive refractor 112 including, for example, a handle that may include a pressure sensor configured to detect when the patient is completing a task, imagining something including, for example, an image, a scene, a memory, and/or a pleasant experience, performing a mental game including, for example, mental mathematics including mental addition and/or subtraction, and/or mental spelling and, in some embodiments, providing the result of the mental game to the wavefront interactive refractor 112, identifying a change in the target 302 and providing an indication of the change to the wavefront interactive refractor 112, identify words and/or images of real objects from a series of images interspersing real words and/or images of real objects with images of nonwords and/or of non-real objects, and/or a target game wherein the patient can manipulate a feature of the target including, for example, changing the target image to achieve the desired outcome. In some embodiments, one or several tasks can be combined into a single task, thus, in one embodiment, for example, the task can comprise reading changing text and/or clicking a button when a word describes a certain type of object is read. A person of skill in the art will recognize that the list 900 does not include all tasks that could be provided by the wavefront interactive refractor 212, and that tasks include any activity, event, and/or action which affects the refractive state of the patient's eye 102.

With reference now to FIG. 10, a list 1000 of target changes is provided. As discussed above, in some embodiments the target 302 can be changed and/or manipulated so as to affect a change in the refractive state of the patient's eye 102. In some embodiments, these changes can be associated with the task as discussed above.

The change of the target 302 can be controlled by a component of the wavefront interactive refractor 112 including, for example, the processor 200, and in some embodiments, the change the target 302 can be controlled by the user and/or patient via the user interface 202 and/or the patient interface 204. The list 1000 of changes to the target 302 can include, for example, a change of the target image such as, for example, changing from a crosshair target 302 to a landscape scene target 302, a change of a feature of the target 302, a change of a color of all or a portion of the target 302. In some embodiments, changing the color of the target can simulate motion of the target 302 as different colors of light focus at different distances in the eye 102.

As seen in FIG. 10, potential changes to the target 302 can further include a change in the shape of all or a portion of the shape of the target 302, a change in the level of contrast of all or a portion of the target 302, a change in the brightness of all or a portion of the target 302, a change in both the brightness and the position of the target 302, a change in the brightness and the focus of the target 302. In some embodiments, change in brightness in connection with a change in another aspect of the target can advantageously take advantage of changes in the refractive state of the eye 102 that can accompany changes in the pupil size of the eye. In some embodiments, for example, the brightness of the target 302 can be varied to affect the refractive state of the eye 302, and in some embodiments, the brightness of the target 302, as well as other aspects of the target 302 can be changed to affect the refractive state of the eye 102. In some embodiments, the brightness of the target can be automatically adjusted based on the level of focus of and/or distance from the target 302, and in some embodiments, the user can control the brightness of the target 302.

In some embodiments, for example, as the focus of the target 302 decreases and/or as the distance to the target 302 increases, the brightness of the target 302 can also be increased to affect a change in the refractive state of the eye 102. As discussed above some pupil sizes can be desired. In such an embodiment, the benefits of increasing the brightness of the target as measured by the increased relaxation of the accommodation of the patient's eye can be weighed against the detriments of increasing the brightness of the target 302 as measured by the decreased pupil diameter.

In some embodiments, the effects of the change in pupil size, such as caused by the change in the brightness of the target 302, can be compensated for in calculating the refractive state of the eye 102. Specifically, for example, the spherical equivalent of the eye 102 varies with pupil diameter, which pupil diameter varies with time. Specifically, in some embodiments, the spherical equivalent of the eye 102 can get very large when the pupil exceeds diameters of, for example, 4 mm, 5 mm, 6 mm or 8 mm. As it may, in some embodiments, be advantageous for the indicator 306 of the refractive state of the eye 102 to display the accomodative state of the eye 102 independent of the size of the pupil, the calculation of the refractive state of the eye 102 can use a corrective aspect to adjust for the varying size of the pupil diameter, especially when the brightness of the target 302 is varied. In some embodiments, for example, this corrective aspect can comprise a Seidel correction that includes the spherical aberration term, and in some embodiments, the calculation can be based on a particular analysis diameter, which diameter can be chosen to be the diameter that provides the best match when comparing the measured refractive state of the eye 102 with the goal parameter associated with the goal indicator 310.

As seen in FIG. 10, potential changes to the target 302 can further include a change in the focus of the target 302, and/or a target 302 comprising video that can include, for example, a object moving advancing from the distance, or receding into the distance, such as, for example, a ball receding into the distance. In some embodiments, for example, multiple changes to the target 302 can occur at once.

A number of variations and modifications of the disclosed embodiments can also be used. Specific details are given in the above description to provide a thorough understanding of the embodiments. However, it is understood that the embodiments may be practiced without these specific details. For example, well-known circuits, processes, algorithms, structures, and techniques may be shown without unnecessary detail in order to avoid obscuring the embodiments.

Implementation of the techniques, blocks, steps and means described above may be done in various ways. For example, these techniques, blocks, steps and means may be implemented in hardware, software, or a combination thereof. For a hardware implementation, the processing units may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the embodiments may be described as a process which is depicted as a flowchart, a flow diagram, a swim diagram, a data flow diagram, a structure diagram, or a block diagram. Although a depiction may describe the operations as a sequential process, many of the operations can be performed in parallel or concurrently. In addition, the order of the operations may be re-arranged. A process is terminated when its operations are completed, but could have additional steps not included in the figure. A process may correspond to a method, a function, a procedure, a subroutine, a subprogram, etc. When a process corresponds to a function, its termination corresponds to a return of the function to the calling function or the main function.

Furthermore, embodiments may be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks may be stored in a machine readable medium such as a storage medium. A code segment or machine-executable instruction may represent a procedure, a function, a subprogram, a program, a routine, a subroutine, a module, a software package, a script, a class, or any combination of instructions, data structures, and/or program statements. A code segment may be coupled to another code segment or a hardware circuit by passing and/or receiving information, data, arguments, parameters, and/or memory contents. Information, arguments, parameters, data, etc. may be passed, forwarded, or transmitted via any suitable means including memory sharing, message passing, token passing, network transmission, etc.

For a firmware and/or software implementation, the methodologies may be implemented with modules (e.g., procedures, functions, and so on) that perform the functions described herein. Any machine-readable medium tangibly embodying instructions may be used in implementing the methodologies described herein. For example, software codes may be stored in a memory. Memory may be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" may represent one or more memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to portable or fixed storage devices, optical storage devices, and/or various other storage mediums capable of storing that contain or carry instruction(s) and/or data.

While the principles of the disclosure have been described above in connection with specific apparatuses and methods, it is to be clearly understood that this description is made only by way of example and not as limitation on the scope of the disclosure.

What is claimed is:

1. A method, comprising:
    a scanning engine repeatedly collecting data, at a first resolution, indicative of a refractive state of a patient's eye over a period of time;
    repeatedly ascertaining a current refractive state of the patient's eye from the repeatedly collected data indicative of the refractive state of the patient's eye;
    continuously displaying an indication of the current refractive state of the patient's eye, the displayed indication of the current refractive state being continuously variable with time;
    while displaying the indication of the current refractive state of the patient's eye, receiving from a user or the patient a command to capture additional data indicative of the refractive state of the patient's eye; and
    in response to the command, the scanning engine capturing additional data, at a second resolution, indicative of the refractive state of the patient's eye, wherein the second resolution is greater than the first resolution; and
    ascertaining a final refractive state of the patient's eye from the captured additional data indicative of the refractive state of the patient's eye.

2. The method of claim 1, wherein the data indicative of the refractive state of the patient's eye is wavefront data sensed by a Shack-Hartmann wavefront sensor.

3. The method of claim 1, further comprising providing an accommodation aid to the patient while the scanning engine repeatedly collects, at the first resolution, data indicative of the refractive state of the patient's eye.

4. The method of claim 1, further comprising, while displaying the indication of the current refractive state of the patient's eye:
    receiving a task request from the user or the patient; and
    in response to the received task request, providing an indicator of a first patient task to be performed by the patient.

5. The method of claim 4, further comprising receiving a patient input in response to the first patient task to be performed.

6. The method of claim 4, further comprising displaying to the patient a target with a changing property.

7. The method of claim 6, wherein the indicator of the first patient task includes a request for a patient input in response to the changing property of the target.

8. The method of claim 6, wherein the changing property includes one of:
    changing a brightness of at least a portion of the target;
    changing a color of at least a portion of the target;
    changing a clarity of at least a portion of the target;
    changing an image of the target; and
    changing a size of the target.

9. The method of claim 4, further comprising:
    receiving a second task request from the user or the patient; and
    in response to the received second task request, providing an indicator of a second patient task to be performed by the patient, the second patient task being different than the first patient task.

10. The method of claim 1, wherein the final refractive state of the patient's eye is ascertained with greater accuracy from the captured additional data indicative of the refractive state of the patient's eye than the current refractive state of the patient's eye is ascertained from the collected data indicative of the refractive state of a patient's eye.

11. A system, comprising:
    a patient interface configured to display a target to a patient;
    a scanning engine configured to obtain data indicative of a refractive state of a patient's eye;
    a display device; and
    a processor configured to:
        cause the scanning engine to repeatedly collect data, at a first resolution, indicative of the refractive state of the patient's eye over a period of time;
        repeatedly ascertain a current refractive state of the patient's eye from the repeatedly collected data indicative of the refractive state of the patient's eye;
        cause the display device to continuously display an indication of the current refractive state of the patient's eye, the displayed indication of the current refractive state being continuously variable with time;
        while displaying the indication of the current refractive state of the patient's eye, receive from a user or the patient a command to capture additional data indicative of the refractive state of the patient's eye; and
        in response to the command, cause the scanning engine to capture additional data, at a second resolution, indicative of the refractive state of the patient's eye, wherein the second resolution is greater than the first resolution; and ascertain a final refractive state of the patient's eye from the captured additional data indicative of the refractive state of the patient's eye.

12. The system of claim 11, wherein the display device is included in the patient interface.

13. The system of claim 11, further comprising a user interface distinct from the patient interface, wherein the display device is included in the user interface.

14. The system of claim 11, wherein the processor is configured to receive the command to capture additional data indicative of the refractive state of the patient's eye via the patient interface.

15. The system of claim 11, further comprising a user interface distinct from the patient interface, wherein the processor is configured to receive the command to capture additional data indicative of the refractive state of the patient's eye via the user interface.

16. The system of claim 11, wherein the scanning engine includes a Shack-Hartmann wavefront sensor.

17. The system of claim 11, wherein the processor is further configured to cause the patient interface to provide an accommodation aid to the patient while the scanning engine repeatedly collects, at the first resolution, data indicative of the refractive state of the patient's eye.

18. The system of claim 11, wherein the processor is further configured to, while the display device displays the indication of the current refractive state of the patient's eye:
  receive a task request from the user or the patient; and
  in response to the received task request, provide an indicator of a patient task to be performed by the patient.

19. The system of claim 18, wherein the processor is further configured to cause the patient interface to display to the patient the target with a changing property.

20. The system of claim 19, wherein the indicator of the patient task includes a request for a patient input in response to the changing property of the target.

* * * * *